United States Patent
Cuzzato

(10) Patent No.: US 6,300,530 B1
(45) Date of Patent: *Oct. 9, 2001

(54) CATALYST FOR THE FLUORINATION OF HALOGENATED ORGANIC COMPOUNDS

(75) Inventor: Paolo Cuzzato, Ponzano Veneto (IT)

(73) Assignee: Ausimont S.p.A., Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 09/305,676

(22) Filed: May 5, 1999

(30) Foreign Application Priority Data

May 7, 1998 (IT) .............................. MI98A0996

(51) Int. Cl.⁷ .................................... C07C 17/08
(52) U.S. Cl. .................... 570/166; 570/167; 570/168; 570/169
(58) Field of Search ................ 570/166, 167, 570/168, 169

(56) References Cited

U.S. PATENT DOCUMENTS

| 4,967,023 | 10/1990 | Carmello et al. | 570/166 |
| 5,008,475 | 4/1991 | Manzer et al. | 570/168 |
| 5,600,039 | 2/1997 | Galland et al. | |
| 5,981,813 * | 11/1999 | Cuzzato | 570/166 |

FOREIGN PATENT DOCUMENTS

| 0 282 005 A1 | 9/1988 | (EP) . |
| 0 298 662 A1 | 1/1989 | (EP) . |
| 0 408 005 B1 | 1/1991 | (EP) . |
| 0 548 742 A1 | 6/1993 | (EP) . |
| 0 609 124 A1 | 8/1994 | (EP) . |
| 0 879 808 A2 | 11/1998 | (EP) . |
| WO 90/08755 | 8/1990 | (WO) . |

* cited by examiner

*Primary Examiner*—Alan Siegel
(74) *Attorney, Agent, or Firm*—Arent Fox Kintner Plotkin Kahn PLLC.

(57) ABSTRACT

Catalyst comprising a supported Cr(III) amorphous compound, characterized in that the support is formed by an aluminum trifluoride ($AlF_3$) having an high surface area obtainable by alumina fluorination with gaseous HF at an initial temperature lower than 300° C., the temperature is rised with a temperature gradient≦100° C./hour up to the final temperature>320° C. and <450° C., the fluorination is continued at the final temperature until feeding a HF molar amount at least equal to the stoichiometric with respect to the alumina, the fluorination being carried out until a fluorinated alumina with a fluorine content not lower than 95% of the stoichiometric is obtained.

4 Claims, No Drawings

CATALYST FOR THE FLUORINATION OF HALOGENATED ORGANIC COMPOUNDS

The present invention relates to the preparation of an improved catalyst for the fluorination of halogenated organic compounds with anhydrous gaseous HF.

More specifically, the present invention relates to a catalyst for the fluorination of HCFC hydrohalocompounds of the 120 and 130 series having higher selectivity and conversion. Specifically those of the 120 series have the general formula $C_2HX_5$ (monohydropentahaloethanes) wherein x equal or different from each other can be either fluorine or chlorine or bromine, provided that there is at least a fluorine atom and an halogen different from fluorine. These compounds are commercially known as HFC/HCFC "120 series".

In particular for the 130 series the general formula is $CF_3CH_2X$ wherein X has the above meaning. These products are commercially well known as products of the 130 series, in particular 133a wherein X=Cl.

Generally the present invention relates to a catalyst for the fluorination of HCFC hydrohalocompounds of the $C_2H_nX_{6-n}$ series wherein x equal or different from each other can be either fluorine or chlorine or bromine, provided that there are at least a fluorine atom and at least an halogen atom different from fluorine, and n is an integer from 1 to 4, preferably it is equal to 1 or 2.

Specifically the catalyst according to the invention is particularly suitable to the synthesis of hydrohalocompounds having 4 or 5 fluorine atoms starting from the corresponding precursors having 3 or 4 fluorine atoms. For the fluorination of the 120 series one specifically refers to the fluorination of 123 having the formula $CHCl_2$—$CF_3$ to obtain 124 having the formula $CHClF$—$CF_3$ and/or 125 of formula $CHF_2$—$CF_3$. For the 130 series the invention preferably relates to the fluorination of 133a having the formula $CH_2Cl$—$CF_3$ to obtain 134a having the formula $CH_2F$—$CF_3$. It is well known the industrial utility to have available efficient catalysts for said reactions, for example for preparing HCFC 123, 124 and 133a and HFC 125 and 134a, not dangerous for the ozone, which replace the chlorofluorocarbons (CFC) banned by the Montreal Protocol: see for instance U.S. Pat. Nos. 4,967,023, 5,008,475, EP 408,005, WO 90/08755.

Most of these processes use a catalyst in heterogeneous phase formed by a compound of the trivalent chromium, sometimes supported on a suitable support such as alumina, aluminum fluoride or carbon.

The fluorination of hydrohalocompounds undergoes kinetic and/or thermodynamic limitations which make it necessary the use of efficient and selective catalysts.

It has been unexpectedly and surprisngly found a catalyst as defined below, its preparation process and a process for the fluorination of halogenated organic compounds with anhydrous gaseous HF capable to operate with high selectivity and conversion.

An object of the present invention is a catalyst comprising a supported Cr(III) amorphous compound, characterized in that the support is formed by an aluminum trifluoride ($AlF_3$) having an high surface area obtainable by alumina fluorination with gaseous HF having a surface area of at least 150 m²/g.

An object of the present invention is therefore a catalyst comprising a supported chromium (III) amorphous compound, characterized in that the support is formed by an aluminum trifluoride $AlF_3$ or fluorinated alumina having an high surface area obtainable by alumina fluorination with gaseous HF having a surface area of at least 150 m²/g, characterized in that the alumina is fluorinated with HF at an initial temperature lower than 300° C., preferably in the range 100°–280° C., still more preferably in the range 150°–200° C., the temperature is rised with a temperature gradient$\leq$100° C./hour up to the final temperature>320° C. and<450° C., preferably in the range 350°–400° C.; then the fluorination is continued at the final temperature until feeding a HF molar amount at least equal to the stoichiometric with respect to the alumina, preferably 1.3 times higher than the stoichiometric, the fluorination being continued until a fluorinated alumina having a fluorine content not lower than 95% of the stoichiometric is obtained.

Preferably the HF flow is diluted with air or inert gas, more preferably air, in volume ratios HF/diluent 0.1:1 to 1:1.

Preferably the thermal gradient is 10°–90° C./hour, more preferably 20°–50° C./hour.

The $AlF_3$ or the fluorinated alumina obtainable with the above process has a surface area higher than that obtainable by direct fluorination of the precursor at the final temperature. According to another aspect of the invention, the alumina to be fluorinated is brought to the initial fluorination temperature and it can be partially fluorinated at this temperature before starting the gradient up to the final temperature, it is then allowed to fluorinate at the final temperature until a fluorinated alumina with a fluorine content not lower than 95% of the stoichiometric is obtained.

The total pressure has no important effects and one generally operates at atmospheric or at slightly higher pressure, generally of some atmospheres.

It is on the contrary advantageous that the HF partial pressure is low, especially at the beginning of the fluorination, to moderate the heat development which could locally increase the temperature over the above limits. Indeed two highly exothermic phenomena contemporaneously occur: the reaction between HF and alumina with formation of $AlF_3$ and water; and the unreacted HF hydration by water. To moderate this exothermic process it is sufficient to use HF diluted with an inert gas in the fluorination conditions, for example, air or nitrogen, with the indicated HF/diluent ratio by volume.

A better control of the temperature is achieved also by carrying out the reaction in a fluidized bed and this is the preferred way to carry out the fluorination. In this case the aluminas to be fluorinated have a particle size distribution compatible with the use of fluidized beds.

When the aluminas are in hydrated form, it is preferable to precede the fluorination with a calcination phase in air or nitrogen, at a temperatures between 300° C. and 400° C. This limits the water development during the reaction, which is undesirable especially as it favours the plants corrosion.

The preferred aluminas for the fluorination have pseudobohemite crystalline structure, surface area of about 300 m²/g.

The aluminas and the aluminum fluorides are characterized by techniques well known to the skilled in the art of the solid characterization: the surface area (SA) is measured by nitrogen adsorption according to the BET method. The analytical composition is obtained by wet way according to known methods.

The aluminas to be fluorinated can optionally comprise up to 15% by weight of silicon oxide, preferably from 1 to 5%.

The chromium amount is in the range from 1 to 20% by weight, preferably from 5 to 15% by weight.

The catalyst preparation can be made with known methods in the art, among which the Applicant has found particularly suitable the one defined by the English term "incipient wetness", hereinafter described. However any other suitable method can of course be used, as known to the skilled in the art of the catalyst preparation.

The preferred general procedure for preparing the catalyst according to the above method comprises the step of impregnating a determined amount of support obtainable with the above described method with a concentrated solution of a Cr(III) soluble salt, for instance chloride. The volume of the impregnating solution is equal to or lower than the volume of the support pores, in order to avoid the adhesion among the granules of the same.

A first drying treatment is then carried out at a moderate temperature—for instance 120° C.—to evaporate water and allow the salt deposition. When necessary, this procedure is repeated many times until the desired amount of metals on the support is reached.

After the final drying the catalyst is transferred into a tubular reactor and calcined for some hours at 300–400° C. in inert gas flow, for example, nitrogen. The final activation is then carried out with a fluorinating agent: an anhydrous HF flow is generally sent into the same reactor and the nitrogen flow is little by little reduced up to the desired HF concentration, which can also be pure HF. Alternatively, the catalyst can be transferred into the fluorination reactor and activated in situ with the same reactant mixture, HF+organic reactants.

A further object of the present invention is a fluorination process of halogenated organic compounds with anhydrous gaseous HF characterized in that the supported chromium catalyst as above defined is used.

Specifically the fluorination process relates to the fluorination of HCFC hydrohalocompounds of the $C_2H_nX_{6-n}$ series wherein X equal or different from each other can be fluorine or chlorine or bromine, provided that there is at least a fluorine atom and at least an halogen atom different from fluorine.

Specifically the fluorination process is suitable to the synthesis of hydrohalocompounds having 4 or 5 fluorine atoms starting from the corresponding precursor having 3 or 4 fluorine atoms. For the 120 series compound fluoriantion, one specifically refers to the fluorination of 123 having the formula $CHCl_2$—$CF_3$ to obtain 124 of formula $CHClF$—$CF_3$ and/or 125 of formula $CHF_2$—$CF_3$. For the 130 series the invention preferably relates to the fluorination of 133a having the formula $CH_2Cl$—$CF_3$ to obtain 134a of formula $CH_2F$—$CF_3$.

In the fluorination processes of halogenated organic compounds the catalysts of the present invention show high conversion and selectivity.

In the fluorination atmospheric or superatmospheric pressures, preferably superatmospheric up to 15 atm, can be used.

By aluminum trifluoride, used as a support, according to the present invention, it is meant the alumina fluorination product, with a fluorine content not lower than 95% of the stoichiometric.

Some example for preparing the particular support, the catalyst and its use in fluorination reactions follow.

EXAMPLES

In all the Examples a commercial alumina CONDEA, precalcined in air flow at 360° C. for 10 hours, is used. The fluorination method is the following: said alumina is loaded, the reactor is heated up to the desired temperature (initial temperature) in air flow, then the HF feeding is started. At this point the temperature gradient starts until the desired maximum temperature (final temperture) is reached. Then it is left at this temperature for the necessary time to feed an HF amount equal to about 1,3 moles of the stoichiometric (the reaction is: $Al_2O_3+6\ HF \rightarrow 2\ AlF_3+3\ H_2O$).

Example 1

(Support Preparation)

180 g of alumina CONDEA SIRAL® 1.5 are introduced in an Inconel® 600 tubular reactor having a 50 mm diameter, electrically heated and equipped with porous septum at the base, heated up to 360° C. in air flow, and fluorinated starting at the temperature of 200° C. which rises up to 360° C. with a 20° C./h gradient, with an air/HF mixture (0.85 moles/h of HF, 4 moles/h of air). It is left at the temperature of 360° C. until a fluorinated alumina having a fluorine content of at least 45% by weight is obtained. It is allowed to cool and about 252 g of aluminum fluoride having the following characteristics:
AS=42.3 $m^2/g$, are discharged.

Example 1A (Catalyst Preparation)

500 g of $AlF_3$ obtained as described in Example 1 are impregnated with 295 cc of a solution prepared by dissolving 324 g of $CrCl_3.6H_2O$ in the necessary water volume.

The so impregnated catalyst is treated in fluidized bed with 100 l/h of nitrogen at 400° C. for 10 hours, then with 100 g/h of anhydrous HF at 360° C. for 24 hours, as above described in the general procedure of the examples. A catalyst containing about 10.5% by weight of chromium (AAS analysis) is thus obtained.

Example 1B (Fluorination of 133a at 320° C.)

60 g of the catalyst prepared in Example 1A are introduced in an Inconel® 600 tubular reactor, having a 50 mm diameter, and heated up to 320° C. in nitrogen flow. At this temperature nitrogen is replaced by anhydrous HF (24 g/h). To HF 59 g/h of 133a are then added, thus achieving a τ contact time of 2.5 s and a HF/133a molar ratio of 4/1. The contact time is meant as the ratio between the reactant volume at the reaction temperature and the apparent volume at stay of the catalyst bed.

The gases flowing out from the reactor are washed to remove the acidity and analyzed by GLC. The following analysis is representative of the obtained results:

| | |
|---|---|
| HFC-134a: | 13.51% molar |
| HCFC-133a | 86.32% molar |
| by-products | 0.17% molar |

The 133a conversion results to be 13.68%, the selectivity in product is equal to 98.8%.

The running is continued for about 50 hours, during which no catalyst decay is noticed and the efficiency and selectivity remain substantially unchanged.

Example 2 Comparative

ESEMPIO 2A Comparative (Support Preparation)

180 g of alumina CONDEA SIRAL® 1.5 are introduced in an Inconel® 600 tubular reactor having a 50 mm diameter, electrically heated and equipped with porous septum at the base, heated up to 360° C. in air flow, and fluorinated for 16 hours with an air/HF mixture (0.85 moles/h of HF, 4 moles/h of air) at the constant temperature of 360° C. It is allowed to cool and about 240 g of aluminum fluoride having the following characteristics:
AS=34.5 m$^2$/g, are discharged.

Example 2B Comparative
(Catalyst Preparation)

The preparation of the catalyst of Example 1A is repeated but using the AlF$_3$ support prepared as in the comparative Example 2A.

Example 2C Comparative
(Fluorination of 133a)

60 g of the catalyst of Example 2B are introduced in the same reactor of Example 1B by using the same fluorination conditions. The following analysis is representative of the obtained results:

| | |
|---|---|
| HFC-134a: | 11.90% molar |
| HCFC-133a | 86.67% molar |
| by-products | 1.43% molar |

The 133a conversion results to be 12.33%, the selectivity in product is equal to 96.5%. As it can be noticed, the activity and the selectivity of the catalyst are lower than those of the invention (Example 1B).

Example 3
(Fluorination of 123)

54 g of the catalyst of Example 1A are introduced in the reactor of Example 1B at the temperature of 300° C. but by feeding 0.58 moles/h of 123 (C$_2$F$_3$HCl$_2$) and 1.676 moles/h of HF achieving a contact time of 2 seconds; the HF/123 molar ratio is equal to 2.85. After 5 hours of running the gases flowing out from the reactor, washed to remove the acidity and analyzed by GLC, gave the following results:

| | |
|---|---|
| HFC-125: | 2.2% molar |
| HCFC-124 | 20.1% molar |
| 123 | 76.6% molar |
| by-products | 1.7% molar |

The 123 conversion results to be 22.4%, the selectivity in products 124+125 is equal to 99.6%.

Example 4
(Fluorination of 123)

Example 3 is repeated but using the catalyst of Example 2 (Example 2B). After 3.5 hours of running the gases flowing out from the reactor, washed to remove the acidity and analyzed by GLC, gave the following results:

| | |
|---|---|
| HFC-125: | 0.7% molar |
| HCFC-124 | 12.0% molar |
| 123 | 87.2% molar |
| by-products | — |

The 123 conversion results to be 12.8%, the selectivity in products 124+125 es equal to 99.2%.

What is claimed is:

1. A catalytic fluorination process of halogenated organic compounds with anhydrous gaseous HF characterized in that the catalyst used comprises a supported Cr(III) amorphous compound, characterized in that the support is formed by an aluminum trifluoride (AlF$_3$) having an high surface area obtainable by fluorination of alumina with gaseous HF having a surface area of at least 150 m$^2$/g, characterized in that the alumina is fluorinated with HF at an initial temperature lower than 300° C., the temperature is rised with a temperature gradient≦100° C./hour up to the final temperature>320° C. and<450° C., the fluorination is continued at the final temperature until feeding a HF molar amount at least equal to the stoichiometric with respect to the alumina, preferably 1.3 times higher than the stoichiometric, the fluorination being carried out until a fluorinated alumina with a fluorine content not lower than 95% of the stoichiometric is obtained.

2. A fluorination process of halogenated organic compounds according to claim 1 wherein the compounds to be fluorinated are HCFC hydrohalocompounds of the C$_2$H$_n$X$_{6-n}$ series wherein X can indifferently be either fluorine or chlorine or bromine, provided that there is at least a fluorine atom and at least an halogen atom different from fluorine, and n is an integer from 1 to 4, preferably it is equal to 1 or 2.

3. A fluorination process of halogenated organic compounds according to claim 2 wherein the compounds to be fluorinated are hydrohalocompounds of the 120 series, preferbly 123 having the formula CHCl$_2$—CF$_3$ to obtain 124 of formula CHClF—CF, and/or 125 having the formula CHF$_2$—CF$_3$.

4. A fluorination process of halogenated organic compounds according to claim 2 wherein the compounds to be fluorinated are hydrohalocompounds of the 130 series, preferably fluorination of 133a having the formula CH$_2$Cl—CF$_3$ to obtain 134a of formula CH$_2$F—CF$_3$.

* * * * *